(12) United States Patent
Sanderson et al.

(10) Patent No.: US 7,182,841 B2
(45) Date of Patent: Feb. 27, 2007

(54) PURIFICATION OF SOLVENTS USED FOR THE PURIFICATION OF ALKYLENE OXIDE

(75) Inventors: John R. Sanderson, Austin, TX (US); Mark Mueller, Austin, TX (US); James P. Farone, Austin, TX (US)

(73) Assignee: Huntsman International LLC, Houston, TX (US)

( * ) Notice: Subject to any disclaimer, the term of this patent is extended or adjusted under 35 U.S.C. 154(b) by 143 days.

(21) Appl. No.: 10/421,367

(22) Filed: Apr. 23, 2003

(65) Prior Publication Data

US 2004/0211658 A1 Oct. 28, 2004

(51) Int. Cl.
*B01D 15/00* (2006.01)
*B01D 11/00* (2006.01)
*B01D 3/34* (2006.01)
*C07C 27/26* (2006.01)

(52) U.S. Cl. ............... 203/41; 203/64; 203/67; 210/638; 210/650; 210/669; 210/195.2; 210/241; 568/872

(58) Field of Classification Search ............ 203/41, 203/64, 67, 43, 46; 210/638, 650, 669, 195.2, 210/241; 568/868
See application file for complete search history.

(56) References Cited

U.S. PATENT DOCUMENTS

| | | | |
|---|---|---|---|
| 2,622,060 A | 12/1952 | Robeson et al. ......... 202/39.5 |
| 3,578,568 A | 5/1971 | Washall .................. 203/64 |
| 3,632,482 A | 1/1972 | Hoory et al. ............. 203/56 |
| 3,881,996 A | 5/1975 | Schmidt .................. 203/71 |
| 5,000,825 A | 3/1991 | Shih et al. ............... 203/3 |
| 5,578,568 A | 11/1996 | Ammons et al. .......... 514/12 |
| 5,785,857 A * | 7/1998 | Kelly et al. ............. 210/638 |
| 5,958,192 A * | 9/1999 | Morford .................. 203/64 |
| 6,187,973 B1 * | 2/2001 | Husain ................... 568/870 |
| 6,242,655 B1 * | 6/2001 | Husain ................... 568/872 |
| 6,329,558 B1 * | 12/2001 | Mohr et al. .............. 568/868 |
| 6,565,753 B1 * | 5/2003 | Holmgren et al. ......... 210/664 |
| 2005/0009695 A1* | 1/2005 | Klumpe et al. ........... 502/310 |

FOREIGN PATENT DOCUMENTS

DE 1668052 * 6/1971

* cited by examiner

*Primary Examiner*—N. Bhat
(74) *Attorney, Agent, or Firm*—O'Keefe, Egan, Peterman & Enders, LLP

(57) ABSTRACT

This invention concerns a process for removing carbonyl-containing impurities from impure extractive distillation solvent such as a glycol, comprising: contacting the impure extractive distillation solvent with an acidic ion exchange resin. The purified extractive distillation solvent can be recycled for use as a solvent in an extractive distillation process that removes impurities from alkylene oxide. The extractive distillation solvent can be ethylene glycol monomethyl ether (EGME) used to purify propylene oxide.

31 Claims, No Drawings

PURIFICATION OF SOLVENTS USED FOR THE PURIFICATION OF ALKYLENE OXIDE

BACKGROUND OF INVENTION

This invention pertains to the purification of solvents, such as glycol ethers, used to remove carbonyl impurities from alkylene oxides such as propylene oxide.

It is known that fresh alkylene glycols and alkylene glycol ethers, such as ethylene glycol monomethyl ether, are very efficient at removing carbonyl species such as formaldehyde, acetaldehyde, acetone, and propionaldehyde from impure propylene oxide. However, as the ethylene glycol monomethyl ether is recycled, these species tend to build up in the recycled ethylene glycol monomethyl ether and it is thus less efficient at removing these carbonyl species.

SUMMARY OF INVENTION

The present invention provides a solution to one or more of the disadvantages and deficiencies described above.

In one broad respect, this invention is a process for removing impurities from impure glycol, comprising: contacting the impure glycol with an acidic ion exchange resin to remove at least a portion of the impurities to form a purified glycol.

This process may be conducted such that the glycol is an alkylene glycol, an alkylene glycol monoalkyl ether, alkylene glycol dialkyl ether, dialkylene glycol monoalkyl ether, a dialkylene glycol dialkyl ether, or combination thereof; such that the contacting occurs at a temperature in the range from about 25° C. to about 50° C.; such that the contacting occurs at atmospheric pressure or superatmospheric pressure; such that the acidic ion exchange resin is a sulfonic acid resin or a carboxylic acid resin or combination thereof; such that the impurities in the impure glycol are carbonyl-containing compounds in an amount of from 0.1 ppm to 5,000 ppm; such that the impure glycol contains from 0.1 ppm to 1000 ppm of formaldehyde; from 0.1 to 1000 ppm of acetaldehyde; from 0.1 ppm to 2000 ppm of acetone, and from 0.1 ppm to 1000 of ppm of propionaldehyde; such that the impurities in the impure glycol comprise formaldehyde, acetaldehyde, acetone, propionaldehyde, or combination thereof; such that the contacting occurs at a flow rate of between 0.1 and 10 mL of impure glycol per hour per mL of acidic ion exchange resin; such that the impure glycol is obtained from a process used to remove impurities from an alkylene oxide by extractive distillation using the glycol as a solvent; such that the process further comprises employing the purified glycol to removed impurities from an alkylene oxide using extractive distillation; such that the acidic ion exchange resin is a sulfonic acid resin that contains at least 4 equivalents/kg of active sites; such that the acidic ion exchange resin is in the form of a resin bed in a column; such that the process further comprises soaking the acidic ion exchange resin with the glycol prior to use; such that n the acidic ion exchange resin is in the form of beads; such that the contacting occurs by pumping the impure glycol through a bed of the acidic ion exchange resin; such that the process is run in a continuous manner; such that at least 80 percent of the impurities are removed from the impure glycol; such that the acidic ion exchange resin is in the form of a resin bed in a column; such that the process further comprises soaking the acidic ion exchange resin with the glycol prior to use; such that n the acidic ion exchange resin is in the form of beads; such that the contacting occurs by pumping the impure glycol through a bed of the acidic ion exchange resin; such that the process is run in a continuous manner; such that at least 80 percent of the impurities are removed from the impure glycol; and any combination thereof.

In another broad respect, this invention is a process useful for removing carbonyl-contacting impurities from impure ethylene glycol monomethyl ether, comprising: contacting the impure ethylene glycol monomethyl ether with a sulfonic acid ion exchange resin to remove at least a portion of the carbonyl-containing impurities to form a purified ethylene glycol monomethyl ether stream.

This invention has a number of advantages. For example, purification of the glycol enables its recycle to, for example, an extractive distillation column used to removed impurities from an alkylene oxide such as propylene oxide. In addition, it should be appreciated that removing the aldehydes and ketones from a glycol using an acidic resin was surprising and unexpected.

DETAILED DESCRIPTION OF THE INVENTION

The glycol purification process of this invention may be conducted in a variety of ways. In general, the impure glycol to be treated is contacted with an acidic ion exchange resin under conditions effective to remove at least a portion of the impurities in the glycol. The process of this invention to reduce impurities of impure glycol can be carried out at a variety of temperatures and pressures. Generally, the temperature at which the contacting of the impure glycol with the acidic ion exchange resin is from 0° C. to 100° C., and in on embodiment is in the range from about 10° C. to about 50° C., and in another embodiment is in the range from about 25° C. to about 50° C. The pressure at which contacting occurs can be atmospheric, subatmospheric, or superatmospheric, and in one embodiment is atmospheric or super atmospheric. Generally the pressure at which the contacting occurs is from about 0 psig (atmospheric) to about 1000 psig. The contacting may occur at higher pressures, but there is generally no particular advantage in doing so. In one embodiment the carbonyl-containing compound impurities are removed at atmospheric pressure at or below about 100 psig.

The flow rate of the impure glycol through the acidic ion exchange resin bed may vary widely, and may be any flow rate which provides for removing impurities from the glycol ether feed. In a commercial operation the flow rate may vary depending, in addition, on the concentration of the impurities in the glycol to be treated. In general the flow rate is from about 0.1 to about 10 mL/hour per mL of (dry) acidic ion exchange resin. In one embodiment, the flow rate is from about 0.5 to about 5 mL/hour per mL of acidic ion exchange resin. In another embodiment, the flow rate is about 1 mL/hour per mL of acidic ion exchange resin. The volume of resin is measured as received, as shown below in the examples, prior to swelling.

Generally, this process is conducted such that the glycol is in the liquid phase; that is, glycol in liquid form is contacted with the acidic ion exchange resin. The process can be run batch-wise, intermittently, or continuously, and is typically conducted in a continuous manner. In a commercial operation, the acidic ion exchange resin may be loaded into a column, pipe, tank or other vessel, and the like in any desired configuration. For example, the acidic ion exchange resin in the form of beads, as are often sold commercially, can be loaded into an upright column in which conventional means are employed to hold the resin in place. The resin can thus comprise a packed bed in a column. In this manner, the impure glycol is usually fed to the top of the resin bed. The glycol can descend through the bed by gravity or may be pumped through the column. Thus in one embodiment, the glycol can be pumped through the bed irrespective of whether the column is vertical, horizontal, or otherwise. In one embodiment, the column is vertical. However, it should be appreciated that the impure glycol can also be fed into the bed, can be fed both above and in the bed, can be fed through multiple points, and so on. Two or more resin beds can be employed in series, in parallel, or any combination thereof. For example, two resin beds may be operated such that one bed is in service while the second bed is being regenerated or changed out with fresh resin. The size, length, diameter, and so on of the resin bed may vary widely depending on the concentration of carbonyl compounds in the stream of impure glycol to be treated.

The alkylene glycols that may be treated in accordance with this invention generally contain less than 20 carbon atoms. Representative examples of such alkylene glycols include but are not limited to ethylene glycol, propylene glycol, and butylene glycol.

The glycol ethers that may be treated in the accordance with this invention generally contain less than 20 carbon atoms. In general, the glycol ethers are alkylene glycol ethers. In one embodiment, the glycol ether is an alkylene glycol monoalkyl ether, an alkylene glycol dialkyl ether, a dialkylene glycol monoalkyl ether, a dialkylene glycol dialkyl ether, or combination thereof. Representative examples of such glycol ethers include but are not limited to ethylene glycol monomethyl ether (EGME), propylene glycol monomethyl ether, butylene glycol monomethyl ether, ethylene glycol monoethyl ether, propylene glycol monoethyl ether, butylene glycol monoethyl ether, ethylene glycol monopropyl ether, propylene glycol monopropyl ether, butylene glycol monopropyl ether, ethylene glycol monobutyl ether, propylene glycol monobutyl ether, butylene glycol monobutyl ether, ethylene glycol dimethyl ether, propylene glycol dimethyl ether, butylene glycol dimethyl ether, ethylene glycol diethyl ether, propylene glycol diethyl ether, butylene glycol diethyl ether, ethylene glycol dipropyl ether, propylene glycol dipropyl ether, butylene glycol dipropyl ether, ethylene glycol dibutyl ether, propylene glycol dibutyl ether, butylene glycol dibutyl ether, diethylene glycol monomethyl ether, dipropylene glycol monomethyl ether, dibutylene glycol monomethyl ether, diethylene glycol monoethyl ether, dipropylene glycol monoethyl ether, dibutylene glycol monoethyl ether, diethylene glycol monopropyl ether, dipropylene glycol monopropyl ether, dibutylene glycol monopropyl ether, diethylene glycol monobutyl ether, dipropylene glycol monobutyl ether, dibutylene glycol monobutyl ether, diethylene glycol dimethyl ether, dipropylene glycol dimethyl ether, dibutylene glycol dimethyl ether, diethylene glycol diethyl ether, dipropylene glycol diethyl ether, dibutylene glycol diethyl ether, diethylene glycol dipropyl ether, dipropylene glycol dipropyl ether, dibutylene glycol dipropyl ether, diethylene glycol dibutyl ether, dipropylene glycol dibutyl ether, and dibutylene glycol dibutyl ether.

The acidic ion exchange resins employed in the practice of this invention are well known. Generally, the acidic ion exchange resin is a sulfonic acid resin, a carboxylic acid resin, or combination thereof. The resin employed is an effective type and used in an effective amount to effect removal of carbonyl-containing impurities in the impure glycol. Representative commercially available acidic ion exchange resins include Amberlyst 15 and Amberlyst 35. These commercially available resins are characterized as being sulfonic acid resins that are sold in the form of beads. These resins are considered to be cation exchange resins. The beads can be of any size and shape. Commercially available beads typically have a spherical shape and typically range in size from 0.25 mm to 1 mm although larger and smaller sizes may be available in some cases. The resins are also available as powders and extrudates in special cases. For a majority of the resins, the building blocks are styrene and divinylbenzene, although some resins are available in which the polymer matrix is based on other monomers such as methacrylic acid, acrylic acid, epichlorohydrin and others. In all cases, the finished products have a crosslinked structure to give water and solvent insolubility and physical strength. Cation exchange resins have anionic groups such as $SO_3^-$, $COO^-$, $PO_3^-$ attached to the polymer matrix, with an $H^+$ counterion.

The sulfonic acid resins are considered to be strongly acidic. Resins generally referred to as weakly acidic resins include the carboxylic acid resins. Weakly acidic resins are not as effective as strongly acidic resins such as the sulfonic resins. The resins can be washed with water or acid prior to use. It may be necessary to wash with water prior to use, but this depends on the resin. Some resins may be furnished as the sodium salt of the acid, which should be treated with acid prior to use to exchange the sodium for a hydrogen cation to thereby form the acidic resin. The acidic resin can be regenerated by treating with an acid (as is known in the art), but the resin may not be as active after the regeneration.

The resin can be macroreticular, macroporous, or gelular. Typically the resin is macroreticular. The acidic resin is typically a highly acidic cation resin. In general, the acidic resin has at least 4 equivalents/kg of active sites, more generally at least 4.5 equivalents/kg. Amberlyst 15 is thought to have at least 4.8 equivalents/kg of active sites, with Amberlyst 35 having at least 5.2 equivalents/kg. The active sites are commonly measured by titration with standard base to determine the concentration of acid sites. By way of example, a resin with two equivalents of active would have one-half the concentration of sulfonic groups on the resin.

As used herein, impure glycol generally refers to glycol that contains organic, carbonyl-containing compounds such as aldehyde and ketone impurities. Typically the carbonyl-containing impurity has 20 carbons or less. Thus, impurity generally refers to an organic compound(s) other than the glycol. Representative examples of such impurities include but are not limited to formaldehyde, propionaldehyde, acetone, acetaldehyde, and combinations of such impurities. In one embodiment, the impurities enter the glycol by use of the glycol as a solvent during extractive distillation to remove such impurities from impure alkylene oxide (an epoxide such as propylene oxide); that is, the alkylene oxide is being purified to reduce impurity levels, and the glycol solvent thereby becomes contaminated with the impurities, thereby purifying the alkylene oxide to be treated. In the practice of this invention, the impure glycols to be treated (prior to contact with the acidic ion exchange resin) will typically contain from 0.1 ppm to 5,000 ppm of carbonyl-containing compounds. The impure glycol may contain from 0.1 ppm to 1000 ppm of formaldehyde. The impure glycol may contain 0.1 to 1000 ppm of acetaldehyde. The impure glycol may contain 0.1 ppm to 2000 ppm of acetone, in one embodiment from 0.1 to 1500 ppm of acetone. The impure glycol may contain 0.1 ppm to 1000 of ppm of propionaldehyde. The impure glycol in one embodiment may contain formaldehyde, propionaldehyde, acetone, and acetaldehyde. In one embodiment, the impure glycol contains from 0.1 ppm to 1000 ppm of formaldehyde, from 0.1 to 1000 ppm of acetaldehyde, from 0.1 ppm to 1000 ppm of acetone, and from 0.1 ppm to 1000 of ppm of propionaldehyde.

In general, while less impurities may of course be removed if desired, the process of this invention may reduce the total amount of carbonyl-containing impurities at least 80 percent, in one embodiment, at least 50 percent in a second embodiment, and at least 20 percent in a third embodiment. If formaldehyde is present in the impure glycol ether, its amount may be reduced at least 80 percent in one embodiment, at least 50 percent, and in a second embodiment, and at least 20 percent in a third embodiment. If propionaldehyde is present in the impure glycol, its amount may be reduced at least 60 percent, in one embodiment, at least 40 percent in a second embodiment, and in a third embodiment at least 20 percent. If acetone is present in the impure glycol ether, its amount may be reduced at least 60 percent in one embodiment, at least 40 percent in a second embodiment, at least 20 percent in a third embodiment. If acetaldehyde is present in the impure glycol ether, its amount may be reduced at least 60 percent in one embodiment, at least 40 percent, and in a second embodiment, and at least 20 percent in a third embodiment.

The percentage removal will depend on the acidic resin used, the concentration of carbonyls in the feed, the presence of other impurities, the temperature, the flow rate, the age of the catalyst, and so on. With a fresh resin and with glycol that has been used once in the extractive distillation, the carbonyl impurities will be removed to a lower level than with carbonyl containing glycol that has been sent through the extractive distillation a number of times.

In general, this invention is also concerned with the purification of alkylene oxide such as ethylene oxide, propylene oxide, and butylene oxide, particularly propylene oxide. Also, this invention concerns a process for removing contaminating quantities of carbonyl compounds such as formaldehyde, acetaldehyde, acetone, and propionaldehyde from propylene oxide. In addition, this invention concerns a method wherein an impure propylene oxide feedstock contaminated with carbonyl-containing compounds and other oxygenates is purified by extractive distillation using recycled glycol ether wherein the recycled glycol ether is obtained by treatment with the acidic ion exchange resin. In particular, this invention details a method wherein an impure propylene oxide contaminated with carbonyl-containing compounds and other oxygenates is purified by extractive distillation using recycled glycol ether which recycled glycol ether has been passed over an acid resin that removes the carbonyl-containing compounds.

The purification of alkylene oxide using glycol ether is known. For example, the use of extractive distillation using glycol ether to remove the impurities in the alkylene oxide is disclosed in U.S. Pat. Nos. 3,578,568 and 5,958,192, both of which are incorporated herein by reference. In general, these purification methods entail subjecting the alkylene oxide to extractive distillation either batch-wise or continuously. The impure alkylene oxide can be introduced into a vessel such as a fractionation column. Generally the impure alkylene oxide is added at or near the bottom of the column. The glycol ether (the extractive distillation solvent) is fed at or near the top of the column. The system is then heated to effect reflux so that extractive distillation results. The bottoms from the column will comprise the glycol ether solvent and at least a portion of the impurities from the alkylene oxide. The so-purified alkylene oxide exits overhead from the top of the tower. The impure glycol ether exiting the bottom of the column can be purified using acidic ion exchange resin as provided herein. Multiple columns (sometimes referred to as towers) can be employed such as described in U.S. Pat. No. 5,958,192, using the process conditions described therein.

The following examples are illustrative of this invention and are not intended to limit the scope of the invention or claims hereto. Unless otherwise denoted all percentages are by weight.

EXAMPLE 1

Acid ion exchange resin (40 mL of Amberlyst-15 beads) that had been dried at 50° C. was charged to a small glass column. The beads were measured out in a graduated cylinder. A sample of ethylene glycol methyl ether (EGME) containing 118.3 ppm formaldehyde, 61.3 ppm acetaldehyde, 1061.7 ppm acetone, and 270 ppm propionaldehyde was pumped upflow through column until all the air was displaced. The column was then allowed to stand overnight so that the resin beads swelled. The EGME was then pumped downflow under ambient conditions (20–25° C. and atmospheric pressure) at the rate indicated in Table 1. The effluent from the column was then analyzed for impurity content. The amounts of formaldehyde, acetaldehyde, acetone, and propionaldehyde are provided in Table 1.

TABLE 1

| Flow Rate (mL/hr) | Hours On Stream | Formaldehyde (ppm) | Acetaldehyde (ppm) | Acetone (ppm) | Propionaldehyde (ppm) |
|---|---|---|---|---|---|
| | | 118.3 (feed) | 61.3 (feed) | 1061.7 (feed) | 270.5 (feed) |
| 42 | 1 | 7.2 | 20.5 | 410.9 | 22.2 |
| 41 | 2 | 5.9 | 16.8 | 514.5 | 38.7 |
| 42 | 3 | 8.1 | 18.4 | 509.2 | 48.0 |
| 43 | 4 | 8.8 | 20.2 | 618.7 | 46.5 |
| 42 | 5 | 9.5 | 22.1 | 670.2 | 48.9 |
| 43 | 7 | 8.9 | 21.7 | 663.9 | 46.9 |
| 41 | 9 | 9.2 | 22.0 | 696.0 | 50.5 |
| 41 | 11 | 10.4 | 23.7 | 792.6 | 52.3 |
| 43 | 13 | 10.4 | 23.5 | 779.7 | 51.9 |
| 44 | 15 | 10.0 | 23.1 | 870.6 | 54.6 |
| 44 | 17 | 11.0 | 18.5 | 588.9 | 41.4 |
| 42 | 19 | 10.6 | 19.6 | 655.1 | 47.0 |
| 44 | 21 | 8.5 | 20.3 | 679.9 | 42.6 |
| 43 | 23 | 7.2 | 17.8 | 608.5 | 35.0 |

TABLE 1-continued

| Flow Rate (mL/hr) | Hours On Stream | Formaldehyde (ppm) | Acetaldehyde (ppm) | Acetone (ppm) | Propionaldehyde (ppm) |
|---|---|---|---|---|---|
| 42 | 25 | 7.7 | 19.1 | 852.5 | 48.1 |
| 41 | 27 | 7.6 | 18.1 | 726.4 | 40.1 |
| 42 | 29 | 6.4 | 15.4 | 510.5 | 39.3 |
| 41 | 31 | 8.4 | 13.6 | 610.5 | 33.6 |
| 43 | 33 | 8.9 | 13.7 | 643.0 | 32.9 |
| 42 | 35 | 11.0 | 14.7 | 742.3 | 38.1 |
| 41 | 37 | 9.8 | 16.5 | 734.2 | 37.3 |
| 40 | 39 | 10.1 | 15.0 | 729.6 | 31.4 |
| 41 | 41 | 11.0 | 14.5 | 806.6 | 45.5 |
| 40 | 43 | 9.0 | 16.4 | 830.4 | 54.0 |
| 41 | 45 | 9.9 | 16.9 | 810.0 | 45.8 |
| 41 | 47 | 9.6 | 14.7 | 482.3 | 44.5 |
| 40 | 49 | 10.7 | 12.6 | 501.4 | 37.8 |
| 40 | 51 | 11.9 | 14.3 | 550.8 | 33.7 |
| 42 | 53 | 9.1 | 16.0 | 630.4 | 38.1 |
| 40 | 55 | 11.7 | 15.7 | 517.9 | 26.9 |
| 41 | 57 | 14.5 | 17.0 | 658.5 | 31.8 |
| 40 | 59 | 11.9 | 18.8 | 819.6 | 45.7 |
| 43 | 61 | 14.8 | 21.0 | 725.2 | 47.0 |
| 41 | 63 | 14.8 | 18.7 | 799.0 | 40.8 |

EXAMPLE 2

In Table 2, the skin temperature is the temperature on the outside of the column. In this example two feed streams were treated, consecutively. The procedure of Example 1 was repeated except that a different feed stream(s) was/were employed. The results are provided in Table 2.

TABLE 2

| Flow Rate | Skin T | Hours | Carbonyl Compounds by, ppm | | | |
|---|---|---|---|---|---|---|
| Flow rate (mL/hr) | Skin Temp. (deg C.) | Hours On Stream | Formaldehyde (ppm) | Acetaldehyde (ppm) | Acetone (ppm) | Propionaldehyde (ppm) |
| | | | 295.7 (1st feed) | 12.7 (1st feed) | 28.4 (1st feed) | 5.5 (1st feed) |
| | | | 287.3 (2d feed) | 10.8 (2d feed) | 22.2 (2d feed) | 5.5 (2d feed) |
| 41 | 25 | 2 | 8.9 | 9.0 | 24.6 | 18.2 |
| 44 | 25 | 4 | 4.7 | 5.6 | 14.1 | 7.5 |
| 43 | 25 | 6 | 4.7 | 5.0 | 12.6 | 7.8 |
| 43 | 25 | 7 | 7.0 | 6.1 | 11.8 | 10.4 |
| 42 | 25 | 9 | 3.2 | 4.8 | 11.5 | 8.2 |
| 42 | 25 | 10 | 3.8 | 5.3 | 11.2 | 9.1 |
| 42 | 25 | 11 | 3.4 | 4.9 | 12.6 | 7.9 |
| 42 | 24 | 14 | 4.0 | 4.7 | 12.7 | 6.4 |
| 41 | 25 | 16 | 4.1 | 5.0 | 13.5 | 6.8 |
| 40 | 23 | 18 | 4.6 | 5.5 | 12.9 | 12.3 |
| 42 | 24 | 19 | 4.0 | 5.6 | 13.4 | 10.9 |
| 41 | 23 | 21 | 4.3 | 5.6 | 14.6 | 12.1 |
| 40 | 22 | 23 | 4.4 | 5.8 | 14.8 | 12.9 |
| 40 | 22 | 25 | 4.5 | 6.0 | 11.3 | 12.2 |
| 38 | 23 | 26 | 5.1 | 6.4 | 14.7 | 13.2 |
| 38 | 24 | 28 | 5.0 | 6.0 | 14.5 | 13.4 |
| 38 | 23 | 31 | 6.3 | 5.9 | 13.1 | 8.8 |
| 39 | 22 | 35 | 6.1 | 5.7 | 12.8 | 8.3 |
| 39 | 21 | 37 | 4.4 | 3.9 | 12.6 | 5.8 |
| 40 | 23 | 39 | 3.9 | 3.3 | 11.7 | 5.2 |
| 41 | 22 | 40 | 2.5 | 3.0 | 8.3 | 3.8 |
| 40 | 22 | 44 | 3.2 | 3.2 | 10.9 | 6.1 |
| 38 | 22 | 45 | 3.2 | 3.0 | 10.4 | 5.3 |
| 38 | 21 | 46 | 2.7 | 2.3 | 9.3 | 4.7 |
| 39 | 22 | 51 | 2.8 | 2.2 | 8.4 | 4.7 |
| 39 | 21 | 52 | 2.1 | 2.1 | 8.5 | 4.6 |
| 41 | 22 | 54 | 2.1 | 2.2 | 8.5 | 4.7 |

TABLE 2-continued

| Flow Rate | Skin T | Hours | Carbonyl Compounds by, ppm | | | |
|---|---|---|---|---|---|---|
| Flow rate (mL/hr) | Skin Temp. (deg C.) | Hours On Stream | Formaldehyde (ppm) | Acetaldehyde (ppm) | Acetone (ppm) | Propionaldehyde (ppm) |
| 39 | 21 | 56 | 2.4 | 2.2 | 8.1 | 4.5 |
| 40 | 21 | 57 | 2.3 | 2.5 | 6.4 | 4.7 |
| 38 | 22 | 62 | 2.3 | 2.2 | 6.7 | 4.6 |
| 39 | 21 | 63 | 1.7 | 2.2 | 6.0 | 4.5 |
| 38 | 22 | 65 | 1.6 | 2.2 | 5.7 | 4.5 |
| 38 | 22 | 67 | 1.7 | 2.1 | 5.3 | 4.4 |
| 37 | 22 | 68 | 1.6 | 2.3 | 3.8 | 2.3 |
| 38 | 22 | 70 | 1.9 | 1.9 | 10.7 | 2.7 |
| 37 | 21 | 72 | 2.0 | 2.2 | 10.9 | 3.0 |
| 38 | 22 | 74 | 2.2 | 2.4 | 11.2 | 3.2 |
| 36 | 21 | 76 | 2.6 | 2.3 | 8.9 | 3.4 |
| 38 | 21 | 77 | 2.4 | 2.4 | 8.0 | 3.5 |
| 37 | 22 | 79 | 2.6 | 2.3 | 8.3 | 3.9 |
| 37 | 22 | 81 | 2.3 | 2.3 | 7.8 | 3.9 |
| 38 | 21 | 83 | 2.2 | 2.2 | 7.3 | 3.9 |
| 38 | 22 | 84 | 2.2 | 2.2 | 4.2 | 2.3 |
| 37 | 21 | 86 | 1.9 | 2.2 | 8.5 | 7.6 |
| 37 | 21 | 89 | 1.9 | 2.0 | 8.0 | 7.7 |
| 38 | 22 | 90 | 2.2 | 2.3 | 5.0 | 4.1 |
| 37 | 22 | 92 | 2.2 | 2.2 | 5.8 | 4.4 |
| 38 | 22 | 95 | 2.2 | 2.3 | 6.7 | 4.3 |
| 39 | 22 | 96 | 2.1 | 2.3 | 6.9 | 4.2 |
| 38 | 22 | 98 | 2.7 | 2.5 | 6.0 | 4.6 |
| 40 | 22 | 100 | 3.2 | 2.7 | 6.3 | 4.5 |
| 41 | 22 | 102 | 3.0 | 2.6 | 5.5 | 4.5 |
| 40 | 21 | 103 | 3.1 | 2.8 | 5.5 | 4.5 |
| 40 | 22 | 103 | 2.9 | 2.7 | 6.1 | 4.7 |
| 39 | 22 | 105 | 2.6 | 2.5 | 5.3 | 4.6 |
| 38 | 21 | 107 | 3.5 | 2.0 | 7.4 | 3.7 |
| 39 | 21 | 108 | 2.4 | 2.0 | 6.5 | 3.5 |
| 40 | 22 | 110 | 2.3 | 1.8 | 7.2 | 3.9 |
| 40 | 22 | 112 | 2.6 | 1.8 | 6.1 | 3.8 |
| 38 | 22 | 114 | 2.8 | 1.9 | 5.6 | 3.7 |
| 39 | 22 | 116 | 1.6 | 2.0 | 7.0 | 4.1 |
| 39 | 24 | 118 | 1.9 | 1.9 | 6.0 | 3.7 |
| 40 | 23 | 120 | 2.2 | 2.1 | 6.7 | 4.0 |
| 40 | 24 | 123 | 2.1 | 2.1 | 5.4 | 3.4 |
| 39 | 24 | 125 | 2.4 | 2.2 | 6.4 | 4.0 |
| 37 | 25 | 127 | 2.5 | 2.2 | 5.8 | 4.0 |
| 37 | 24 | 129 | 2.8 | 2.5 | 6.5 | 4.4 |
| 37 | 24 | 131 | 2.8 | 2.5 | 6.1 | 4.1 |
| 38 | 24 | 133 | 2.7 | 2.4 | 6.0 | 4.4 |
| 37 | 23 | 125 | 2.4 | 2.4 | 5.9 | 4.2 |
| 38 | 24 | 137 | 2.3 | 2.1 | 5.8 | 4.3 |
| 37 | 24 | 137 | 1.9 | 2.0 | 5.6 | 4.3 |
| 38 | 24 | 139 | 1.7 | 1.9 | 5.7 | 4.5 |
| 39 | 23 | 141 | 1.6 | 1.8 | 5.4 | 4.4 |
| 38 | 23 | 143 | 1.7 | 1.9 | 4.7 | 4.6 |
| 38 | 23 | 144 | 1.5 | 2.0 | 5.0 | 4.0 |
| 37 | 23 | 146 | 1.5 | 2.0 | 5.2 | 4.6 |
| 37 | 24 | 148 | 1.6 | 1.7 | 9.0 | 3.2 |
| 38 | 23 | 149 | 1.8 | 2.0 | 9.1 | 3.5 |
| 39 | 23 | 151 | 1.6 | 1.9 | 8.6 | 3.5 |
| 37 | 22 | 155 | 1.9 | 1.9 | 8.6 | 3.0 |
| 39 | 22 | 156 | 2.1 | 2.0 | 5.6 | 2.3 |
| 38 | 23 | 160 | 2.0 | 2.0 | 8.9 | 3.2 |
| 38 | 22 | 162 | 2.0 | 2.0 | 8.7 | 3.4 |
| 37 | 23 | 164 | 1.9 | 1.9 | 8.3 | 3.6 |
| 39 | 22 | 166 | 1.6 | 1.8 | 7.6 | 3.5 |
| 46 | 23 | 168 | 1.9 | 1.6 | 8.7 | 2.6 |
| 39 | 23 | 170 | 1.7 | 1.8 | 9.5 | 2.7 |
| 39 | 23 | 172 | 1.6 | 1.7 | 9.2 | 2.8 |
| 40 | 22 | 174 | 1.6 | 1.7 | 7.6 | 2.8 |
| 42 | 22 | 176 | 2.0 | 1.9 | 9.6 | 3.2 |
| 41 | 23 | 178 | 2.3 | 2.1 | 9.6 | 3.5 |
| 41 | 22 | 180 | 2.4 | 2.3 | 9.4 | 3.6 |
| 40 | 22 | 182 | 2.5 | 2.3 | 9.6 | 3.7 |
| 38 | 22 | 184 | 2.6 | 2.2 | 8.4 | 3.9 |
| 39 | 22 | 186 | 2.6 | 2.4 | 9.2 | 4.1 |
| 40 | 22 | 188 | 2.7 | 2.0 | 5.7 | 1.1 |
| 41 | 22 | 190 | 2.8 | 2.0 | 10.2 | 2.3 |
| 42 | 22 | 192 | 2.8 | 1.8 | 8.8 | 2.0 |
| 41 | 22 | 193 | 2.0 | 1.8 | 9.8 | 2.5 |

TABLE 2-continued

| Flow Rate | Skin T | Hours | Carbonyl Compounds by, ppm | | | |
|---|---|---|---|---|---|---|
| Flow rate (mL/hr) | Skin Temp. (deg C.) | Hours On Stream | Formal-dehyde (ppm) | Acetal-dehyde (ppm) | Acetone (ppm) | Propion-aldehyde (ppm) |
| 42 | 22 | 195 | 2.7 | 1.8 | 9.3 | 1.9 |
| 42 | 22 | 197 | 2.8 | 1.9 | 10.6 | 2.3 |
| 42 | 21 | 199 | 2.5 | 1.9 | 10.1 | 2.4 |
| 41 | 22 | 201 | 2.4 | 2.0 | 10.5 | 2.5 |
| 41 | 22 | 203 | 2.4 | 1.6 | 8.3 | 1.6 |
| 41 | 21 | 205 | 2.0 | 1.6 | 9.4 | 2.0 |
| 42 | 22 | 207 | 2.1 | 1.6 | 7.9 | 1.8 |
| 41 | 22 | 209 | 2.1 | 1.7 | 9.1 | 2.2 |
| 40 | 22 | 213 | 2.1 | 1.6 | 10 | 2.8 |
| 41 | 21 | 215 | 2.2 | 1.6 | 9.9 | 2.8 |
| 40 | 22 | 217 | 2.1 | 1.6 | 9.4 | 2.7 |
| 40 | 22 | 218 | 2.0 | 1.7 | 10.1 | 2.5 |
| 39 | 21 | 220 | 2.0 | 1.6 | 8.6 | 2.3 |
| 41 | 22 | 222 | 2.5 | 1.9 | 10.1 | 3.3 |
| 40 | 22 | 224 | 2.5 | 2.0 | 10.8 | 3.3 |
| 42 | 21 | 225 | 3.0 | 2.1 | 9.5 | 3.5 |
| 41 | 22 | 227 | 2.7 | 1.9 | 10.2 | 3.2 |
| 41 | 21 | 228 | 2.5 | 2.3 | 6.7 | 2.8 |
| 40 | 22 | 230 | 2.6 | 1.8 | 6.4 | 3.2 |
| 41 | 22 | 232 | 2.5 | 1.9 | 7.2 | 3.4 |
| 41 | 22 | 234 | 2.3 | 1.8 | 7.8 | 3.4 |
| 40 | 21 | 235 | 2.1 | 1.9 | 7.6 | 3.9 |
| 41 | 21 | 237 | 1.7 | 1.8 | 7.6 | 3.9 |
| 43 | 22 | 239 | 1.9 | 1.7 | 6.5 | 3.7 |
| 43 | 22 | 241 | 1.6 | 1.4 | 6.6 | 3.5 |
| 42 | 21 | 242 | 1.6 | 1.6 | 6.0 | 3.7 |
| 42 | 22 | 244 | 1.5 | 1.7 | 5.8 | 3.7 |
| 40 | 22 | 246 | 3.0 | 2.1 | 9.5 | 3.5 |
| 43 | 21 | 247 | 1.7 | 1.5 | 9.3 | 2.9 |
| 42 | 21 | 249 | 1.9 | 1.6 | 8.5 | 3.0 |
| 42 | 21 | 251 | 1.9 | 1.6 | 9.4 | 3.3 |
| 44 | 22 | 253 | 2.1 | 1.7 | 9.4 | 3.3 |
| 44 | 21 | 254 | 2.0 | 1.7 | 9.0 | 3.4 |
| 43 | 21 | 256 | 2.0 | 1.7 | 8.6 | 3.5 |
| 44 | 22 | 258 | 2.9 | 4.2 | 4.6 | 6.7 |
| 43 | 22 | 259 | 2.7 | 4.9 | 5.1 | 4.9 |
| 44 | 22 | 260 | 2.1 | 4.3 | 4.1 | 6.2 |
| 44 | 21 | 262 | 2.6 | 4.7 | 5.5 | 6.9 |
| 45 | 22 | 263 | 2.7 | 4.6 | 4.5 | 6.2 |
| 43 | 22 | 264 | 2.0 | 4.4 | 4.2 | 6.6 |
| 43 | 22 | 266 | 2.5 | 4.4 | 4.4 | 6.7 |
| 44 | 22 | 267 | 2.7 | 4.6 | 4.3 | 5.9 |
| 43 | 22 | 369 | 2.7 | 4.5 | 5.3 | 6.6 |
| 44 | 22 | 271 | 2.9 | 4.6 | 5.4 | 6.8 |
| 44 | 22 | 272 | 2.7 | 4.6 | 4.3 | 6.0 |
| 43 | 22 | 274 | 2.7 | 4.7 | 5.4 | 6.8 |
| 43 | 22 | 276 | 2.8 | 4.6 | 5.4 | 6.5 |
| 43 | 21 | 277 | 15.6 | 4.7 | 6.7 | 10.0 |
| 40 | 22 | 279 | 3.5 | 4.6 | 7.8 | 10.8 |
| 41 | 21 | 281 | 3.6 | 4.2 | 8.2 | 11.3 |
| 41 | 21 | 282 | 2.1 | 3.8 | 6.2 | 9.5 |
| 40 | 21 | 284 | 2.8 | 3.7 | 6.8 | 11.1 |
| 40 | 22 | 286 | 2.6 | 3.9 | 7.2 | 11.2 |
| 36 | 22 | 288 | 2.8 | 4.2 | 8.0 | 11.9 |
| 37 | 21 | 313 | 2.7 | 1.4 | 9.8 | 2.6 |
| 38 | 22 | 316 | 2.1 | 1.3 | 9.7 | 2.4 |
| 39 | 22 | 319 | 2.0 | 1.2 | 9.3 | 3.5 |
| 41 | 21 | 337 | 2.7 | 1.4 | 10.7 | 5.3 |
| 42 | 22 | 339 | 2.6 | 1.4 | 9.7 | 3.0 |
| 41 | 21 | 343 | 2.8 | 1.4 | 9.0 | 2.9 |
| 40 | 20 | 360 | 3.9 | 1.6 | 11.6 | 5.2 |
| 38 | 20 | 369 | 3.5 | 1.7 | 11.5 | 6.1 |
| 40 | 20 | 384 | 3.0 | 1.6 | 10.8 | 5.3 |
| 40 | 20 | 393 | 2.7 | 1.7 | 9.9 | 2.2 |
| 40 | 20 | 395 | 2.1 | 1.5 | 9.5 | 2.1 |
| 40 | 20 | 404 | 2.7 | 1.4 | 9.4 | 2.0 |
| Average | | | 2.7 | 2.7 | 8.4 | 4.9 |
| Removal % | | | 99.1 | 78.7 | 70.5 | 11.0 |

It is believed that the data points for acetaldehyde greater than 5.5 ppm were likely erroneous.

EXAMPLE 3

The procedure of Example 2 was repeated except that Amberlyst 35 as the acidic ion exchange resin and a different feed stream were employed. The results are provided in Table 3.

TABLE 3

| Flow rate (mL/hr) | Temp. (deg. C.) | Hours on stream | Formaldehyde (ppm) | Acetaldehyde (ppm) | Acetone (ppm) | Propionaldehyde (ppm) |
|---|---|---|---|---|---|---|
| | | | 95.5 | 52.9 | 532.9 | 182.4 |
| 43 | 20–25 | 1 | 24.6 | 29.5 | 448.7 | 47.3 |
| 43 | 20–25 | 2 | 25.1 | 28.6 | 449.0 | 47.6 |
| 42 | 20–25 | 3 | 10.9 | 18.8 | 233.3 | 42.2 |
| 44 | 20–25 | 4 | 11.2 | 20.7 | 221.6 | 38.5 |
| 49 | 20–25 | 5 | 74.1 | 34.3 | 347.2 | 91.3 |
| 55 | 20–25 | 6 | 44.8 | 31.8 | 353.8 | 64.3 |
| 50 | 20–25 | 7 | 14.9 | 23.3 | 233.1 | 74.6 |
| 48 | 20–25 | 8 | 19.0 | 26.2 | 282.2 | 67.2 |
| 46 | 20–25 | 9 | 21.9 | 28.2 | 310.8 | 44.5 |
| 44 | 20–25 | 10 | 22.9 | 29.2 | 340.2 | 56.4 |
| 43 | 20–25 | 13 | 25.0 | 32.5 | 383.4 | 51.0 |
| 44 | 20–25 | 15 | 26.4 | 26.8 | 285.0 | 45.5 |
| 42 | 20–25 | 17 | 26.1 | 28.1 | 269.1 | 62.1 |
| 43 | 20–25 | 19 | 35.1 | 31.3 | 349.0 | 49.7 |
| 41 | 20–25 | 21 | 39.6 | 34.0 | 365.0 | 52.3 |
| 39 | 20–25 | 23 | 40.9 | 33.5 | 354.9 | 50.4 |
| 39 | 20–25 | 25 | 36.9 | 33.9 | 384.0 | 56.1 |
| 38 | 20–25 | 27 | 36.7 | 33.2 | 381.4 | 59.4 |
| 39 | 20–25 | 29 | 37.6 | 34.2 | 388.0 | 56.5 |
| 39 | 20–25 | 31 | 37.3 | 34.0 | 344.7 | 53.4 |
| Average | | | 30.6 | 29.6 | 336.2 | 55.5 |
| Removal % | | | 68.0 | 44.0 | 36.9 | 69.6 |

EXAMPLE 4

The procedure of Example 1 was repeated except that the feed stream contained 118.3 ppm of formaldehyde, 61.3 ppm of acetaldehyde, 1061.7 ppm of acetone, and 270.5 ppm of propionaldehyde. The results are provided in Table 4.

TABLE 4

| Flow rate (mL/hr) | Hours on stream | Temp. (Deg. C.) | Formaldehyde (ppm) | Acetaldehyde (ppm) | Acetone (ppm) | Propionaldehyde (ppm) |
|---|---|---|---|---|---|---|
|  |  |  | 118.3 (feed) | 61.3 (feed) | 1061.7 (feed) | 270.5 (feed) |
| 42 | 1 | 25 | 15.0 | 17.9 | 881.9 | 41.9 |
| 42 | 2 | 25 | 9.8 | 15.5 | 809.8 | 36.2 |
| 43 | 3 | 25 | 6.4 | 13.4 | 937.7 | 48.7 |
| 42 | 4 | 25 | 6.2 | 15.9 | 926.4 | 46.8 |
| 41 | 5 | 25 | 4.2 | 12.4 | 907.5 | 41.6 |
| 40 | 6 | 50 | 4.3 | 12.6 | 754.9 | 33.4 |
| 41 | 7 | 59 | 10.7 | 29.3 | 929.5 | 52.9 |
| 40 | 8 | 61 | 13.2 | 19.4 | 922.5 | 54.1 |
| 42 | 9 | 66 | 13.0 | 24.2 | 968.2 | 47.3 |
| 41 | 10 | 67 | 8.0 | 26.4 | 959.5 | 61.5 |
| 40 | 11 | 64 | 8.1 | 28.1 | 976.4 | 57.6 |
| 41 | 12 | 65 | 7.1 | 27.3 | 1065.8 | 61.0 |
| 40 | 13 | 62 | 8.6 | 21.3 | 602.0 | 44.6 |
| 38 | 14 | 60 | 7.9 | 23.6 | 692.3 | 49.2 |
| 40 | 15 | 61 | 6.3 | 26.8 | 1038.7 | 66.5 |
| 41 | 16 | 63 | 6.5 | 22.7 | 699.4 | 45.6 |
| 40 | 17 | 59 | 6.7 | 20.9 | 711.0 | 40.6 |
| 42 | 18 | 61 | 6.9 | 29.0 | 790.1 | 58.0 |
| 42 | 19 | 57 | 7.1 | 26.4 | 776.2 | 55.5 |
| 40 | 20 | 62 | 8.8 | 26.8 | 905.1 | 62.8 |
| Average |  |  | 8.2 | 22.0 | 862.7 | 50.3 |
| Removal % |  |  | 93.0% | 64.1% | 18.7% | 81.4% |

EXAMPLE 5

Comparative Example—Not an Embodiment of the Invention

The procedure of Example 1 was repeated except that Ambersorb 572 resin was used. Ambersorb 572 is a nonionic polymeric adsorbent. The results are provided in Table 5.

TABLE 5

| Temp. Temp. (deg. C.) | Hours Hours on stream | Carbonyl Compounds, ppm ||||
|---|---|---|---|---|---|
|  |  | Formaldehyde (ppm) | Acetaldehyde (ppm) | Acetone (ppm) | Propionaldehyde (ppm) |
|  |  | 104.7 | 37.4 | 355.2 | 192.3 |
| 20–25 | 1 | 106.0 | 42.1 | 364.7 | 228.7 |
| 20–25 | 2 | 106.9 | 45.5 | 296.8 | 194.7 |
| 20–25 | 3 | 105.5 | 43.2 | 389.9 | 198.0 |
| 20–25 | 4 | 106.7 | 47.9 | 458.5 | 196.1 |
| 20–25 | 5 | 106.9 | 49.4 | 498.9 | 202.8 |
| 20–25 | 6 | 106.1 | 50.6 | 511.7 | 200.5 |
| 20–25 | 7 | 106.8 | 51.4 | 518.4 | 199.5 |
| 20–25 | 8 | 108.1 | 52.6 | 534.5 | 205.4 |

The results in Table 5 show that the Ambersorb 572 does not function as a useful resin in the practice of this invention. While not wishing to be bound by theory, it is believed that Ambersorb 572 did not function to remove impurities from the glycol ether because it does not contain the sulfonic acid group. It was not known why the impurities increased over time.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A process for removing carbonyl-containing impurities from impure glycol, comprising: contacting the impure glycol with an acidic ion exchange resin to remove at least a portion of the carbonyl-containing impurities to form a purified glycol, wherein the carbonyl-containing impurities are selected from the group consisting of aldehydes, ketones, or both, employing the purified glycol to remove impurities from an alkylene oxide using extractive distillation, and employing the purified glycol to remove impurities from an alkylene oxide using extractive distillation.

2. The process of claim 1, wherein glycol is an alkylene glycol, alkylene glycol monoalkyl ether, alkylene glycol dialkyl ether, dialkylene glycol monoalkyl ether, a dialkylene glycol dialkyl ether, or combination thereof.

3. The process of claim 1, wherein the glycol is ethylene glycol, propylene glycol, butylene glycol, ethylene glycol monomethyl ether, propylene glycol monomethyl ether, butylene glycol monomethyl ether, ethylene glycol monoethyl ether, propylene glycol monoethyl ether, butylene glycol monoethyl ether, ethylene glycol monopropyl ether, propylene glycol monopropyl ether, butylene glycol monopropyl ether, ethylene glycol monobutyl ether, propylene glycol monobutyl ether, butylene glycol monobutyl ether, ethylene glycol dimethyl ether, propylene glycol dimethyl ether, butylene glycol dimethyl ether, ethylene glycol diethyl ether, propylene glycol diethyl ether, butylene glycol diethyl ether, ethylene glycol dipropyl ether, propylene glycol dipropyl ether, butylene glycol dipropyl ether, ethylene glycol dibutyl ether, propylene glycol dibutyl ether, butylene glycol dibutyl ether, diethylene glycol monomethyl ether, dipropylene glycol monomethyl ether, dibutylene glycol monomethyl ether, diethylene glycol monoethyl ether, dipropylene glycol monoethyl ether, dibutylene glycol monoethyl ether, diethylene glycol monopropyl ether, dipropylene glycol monopropyl ether, dibutylene glycol monopropyl ether, diethylene glycol monobutyl ether, dipropylene glycol monobutyl ether, dibutylene glycol monobutyl ether, diethylene glycol dimethyl ether, dipropylene glycol dimethyl ether, dibutylene glycol dimethyl ether, diethylene glycol diethyl ether, dipropylene glycol diethyl ether, dibutylene glycol diethyl ether, diethylene glycol dipropyl ether, dipropylene glycol dipropyl ether, dibutylene glycol dipropyl ether, diethylene glycol dibutyl ether, dipropylene glycol dibutyl ether, dibutylene glycol dibutyl ether, and combinations thereof.

4. The process of claim 1, wherein the glycol is ethylene glycol monomethyl ether.

5. The process of claim 1, wherein the contacting occurs at a temperature in the range from about 25° C. to about 50° C.

6. The process of claim 1, wherein the contacting occurs at atmospheric pressure or superatmospheric pressure.

7. The process of claim 1, wherein the acidic ion exchange resin is a sulfonic acid resin.

8. The process of claim 1, wherein the acidic ion exchange resin is a sulfonic acid resin that contains at least 4 equivalents/kg of active sites.

9. The process of claim 1, wherein the impurities in the impure glycol are carbonyl-containing compounds in an amount of from 0.1 ppm to 5,000 ppm.

10. The process of claim 1 wherein the impure glycol contains from 0.1 ppm to 1000 ppm of formaldehyde; from 0.1 to 1000 ppm of acetaldehyde; from 0.1 ppm to 2000 ppm of acetone, and from 0.1 ppm to 1000 of ppm of propionaldehyde.

11. The process of claim 1, wherein the impurities in the impure glycol comprise formaldehyde, acetaldehyde, acetone, propionaldehyde, or combination thereof.

12. The process of claim 1, wherein the contacting occurs at a flow rate of between 0.1 and 10 mL of impure glycol per hour per mL of acidic ion exchange resin.

13. The process of claim 1, wherein the acidic ion exchange resin is in the form of a resin bed in a column.

14. The process of claim 1, further comprising soaking the acidic ion exchange resin with the glycol prior to use.

15. The process of claim 1, wherein the acidic ion exchange resin is in the form of beads.

16. The process of claim 1, wherein the contacting occurs by pumping the impure glycol through a bed of the acidic ion exchange resin.

17. The process of claim 1, wherein the process is run in a continuous manner.

18. The process of claim 1, wherein at least 80 percent of the impurities are removed from the impure glycol.

19. A process useful for removing an aldehyde, a ketone, or both from impure ethylene glycol monomethyl ether, comprising: contacting the impure ethylene glycol monomethyl ether with a sulfonic acid ion exchange resin to remove at least a portion of the aldehyde, the ketone, or both to form a purified ethylene glycol monomethyl ether stream, employing the purified ethylene glycol monomethyl ether to remove impurities from an alkylene oxide using extractive distillation, and employing the purified ethylene glycol monomethyl ether to remove impurities from an alkylene oxide using extractive distillation.

20. The process of claim 19, wherein the contacting occurs at a temperature in the range from about 25° C. to about 50° C.

21. The process of claim 19, wherein the contacting occurs at atmospheric pressure or superatmospheric pressure.

22. The process of claim 19, wherein the aldehyde, the ketone or both in the impure ethylene glycol monomethyl ether is present in an amount of from 0.1 ppm to 5,000 ppm.

23. The process of claim 19, wherein the impure ethylene glycol monomethyl ether contains from 0.1 ppm to 1000 ppm of formaldehyde; from 0.1 to 1000 ppm of acetaldehyde; from 0.1 ppm to 2000 ppm of acetone, and from 0.1 ppm to 1000 of ppm of propionaldehyde.

24. The process of claim 19, wherein the aldehyde, the ketone or both in the impure ethylene glycol monomethyl ether comprise formaldehyde, acetaldehyde, acetone, propionaldehyde, or combination thereof.

25. The process of claim 19, wherein the contacting occurs at a flow rate of between 0.1 and 10 mL of impure glycol per hour per mL of acidic ion exchange resin.

26. The process of claim 19, wherein the acidic ion exchange resin is in the form of a resin bed in a column.

27. The process of claim 19, further comprising soaking the acidic ion exchange resin with the ethylene glycol monomethyl ether prior to use.

28. The process of claim 19, wherein the acidic ion exchange resin is in the form of beads.

29. The process of claim 19, wherein the contacting occurs by pumping the impure ethylene glycol monomethyl ether through a bed of the acidic ion exchange resin.

30. The process of claim 19, wherein the process is run in a continuous manner.

31. The process of claim 19, wherein at least 80 percent of the aldehyde, the ketone or both is removed from the impure ethylene glycol monomethyl ether.

* * * * *